(12) United States Patent
Rittner et al.

(10) Patent No.: US 9,649,514 B2
(45) Date of Patent: May 16, 2017

(54) CHEMICAL OXYGEN GENERATOR WITH BIMETAL REACTION CONTROL

(71) Applicant: Zodiac Aerotechnics, Plaisir (FR)

(72) Inventors: Wolfgang Rittner, Ahrensbok (DE); Rüdiger Meckes, Berkenthin (DE); Günter Boomgaarden, Scharbeutz (DE); Marco Hollm, Rosdorf (DE)

(73) Assignee: Zodiac Aerotechnics, Plaisir (FR)

( * ) Notice: Subject to any disclaimer, the term of this patent is extended or adjusted under 35 U.S.C. 154(b) by 419 days.

(21) Appl. No.: 13/929,823

(22) Filed: Jun. 28, 2013

(65) Prior Publication Data

US 2014/0000592 A1 Jan. 2, 2014

Related U.S. Application Data

(60) Provisional application No. 61/665,486, filed on Jun. 28, 2012.

(51) Int. Cl.
*A62B 9/02* (2006.01)
*A62B 21/00* (2006.01)
(Continued)

(52) U.S. Cl.
CPC ............... *A62B 7/08* (2013.01); *A61M 16/20* (2013.01); *A62B 7/00* (2013.01); *A62B 7/02* (2013.01); *A62B 7/14* (2013.01); *A62B 9/02* (2013.01); *A62B 18/02* (2013.01); *A62B 21/00* (2013.01); *B64D 10/00* (2013.01); *B64D 11/0015* (2013.01); *B64D 11/00155* (2014.12); *B64D 2231/00* (2013.01); *B64D 2231/02* (2013.01);

(Continued)

(58) Field of Classification Search
USPC ....... 422/120, 122, 195, 197, 631, 633, 636, 422/648, 651
See application file for complete search history.

(56) References Cited

U.S. PATENT DOCUMENTS 2,450,289 A * 9/1948 Marek .................... B01D 53/02
422/120
3,326,212 A * 6/1967 Phillips .................... A62B 7/06
128/201.21

(Continued)

OTHER PUBLICATIONS

Google search—burning temperature of chlorate candle with iron (results attached).*

(Continued)

*Primary Examiner* — Jackie Tan-Uyen T Ho
*Assistant Examiner* — Joseph D Boecker
(74) *Attorney, Agent, or Firm* — Hodgson Russ LLP

(57) ABSTRACT

The invention relates to a regulation device for a source of breathable gas, comprising a reaction medium adapted to perform an exothermic reaction for the production of breathable gas, the reaction medium surrounding an interior reaction volume having a breathable gas outlet. The invention further relates to a chemical oxygen generator system for the provision of breathable gas in an aircraft as well as to a method for regulating a source of breathable gas comprising the step of initiating an exothermic reaction of a reaction medium for the production of breathable gas, the reaction medium surrounding an interior reaction volume having a breathable gas outlet, wherein the breathable gas is flowing through the breathable gas outlet.

19 Claims, 1 Drawing Sheet

(51) Int. Cl.
- *A62B 7/08* (2006.01)
- *A61M 16/20* (2006.01)
- *A62B 7/00* (2006.01)
- *B64D 11/00* (2006.01)
- *A62B 7/02* (2006.01)
- *A62B 7/14* (2006.01)
- *A62B 18/02* (2006.01)
- *B64D 10/00* (2006.01)
- *G08B 5/22* (2006.01)
- *G08B 5/00* (2006.01)
- *G08B 5/36* (2006.01)

(52) U.S. Cl.
CPC ............... *G08B 5/00* (2013.01); *G08B 5/224* (2013.01); *G08B 5/36* (2013.01)

(56) References Cited

U.S. PATENT DOCUMENTS

| | | | | |
|---|---|---|---|---|
| 3,756,785 A | * | 9/1973 | Netteland | A62B 21/00 128/202.26 |
| 4,016,878 A | * | 4/1977 | Castel | A61M 16/1075 126/204 |
| 4,111,661 A | * | 9/1978 | Rothenberger | B01J 7/00 414/292 |
| 4,154,236 A | * | 5/1979 | Eckstein | A62B 7/08 128/202.26 |
| 4,213,453 A | * | 7/1980 | Warncke | A62B 7/08 128/202.26 |
| 4,409,978 A | * | 10/1983 | Bartos | A62B 7/10 128/202.26 |
| 4,515,156 A | * | 5/1985 | Khudosovtsev | A62B 21/00 128/202.26 |
| 4,662,352 A | * | 5/1987 | Aviles, Jr. | A61M 16/1075 126/204 |
| 4,764,346 A | * | 8/1988 | Lewis | A61M 16/0057 128/204.28 |
| 4,891,189 A | * | 1/1990 | Harwood, Jr. | B01J 7/00 102/530 |
| 5,042,471 A | * | 8/1991 | Drews | A62B 7/08 128/202.26 |
| 5,222,479 A | * | 6/1993 | Brauer | A62B 7/08 128/202.26 |
| 5,288,469 A | * | 2/1994 | Skalla | A61B 18/00 261/DIG. 26 |
| 5,357,758 A | * | 10/1994 | Andonian | A62B 7/06 62/45.1 |
| 6,062,210 A | * | 5/2000 | Welles | F24J 1/00 126/208 |
| 6,485,451 B1 | * | 11/2002 | Roberts | A61M 1/0058 236/101 C |
| 6,761,162 B1 | * | 7/2004 | Swann | A62B 23/06 128/201.25 |
| 6,814,944 B1 | * | 11/2004 | Matsui | B01J 8/0214 422/198 |
| 7,052,656 B2 | * | 5/2006 | Engeler | B01D 3/20 202/156 |
| 7,314,501 B2 | * | 1/2008 | Fayard | F01N 3/0214 55/282.2 |
| 2003/0164171 A1 | * | 9/2003 | Andersen | A62B 9/006 128/204.26 |
| 2004/0151639 A1 | * | 8/2004 | Jones | A62B 21/00 422/120 |
| 2008/0237131 A1 | * | 10/2008 | Brown | B01D 53/0438 210/656 |
| 2013/0192596 A1 | * | 8/2013 | Rittner | A62B 7/08 128/202.26 |

OTHER PUBLICATIONS

David Blake, "The Response of Aircraft Oxygen Generators Exposed to Elevated Temperatures", U.S. Department of Transportation, Federal Aviation Administration, Apr. 2003, DOT/FAA/AR-TN03/35.*

First Office Action for Chinese Patent Application No. CN 20130269137.2, mailed Apr. 14, 2016, 9 pages (4 pages for Chinese Office Action, 5 pages for English translation).

* cited by examiner

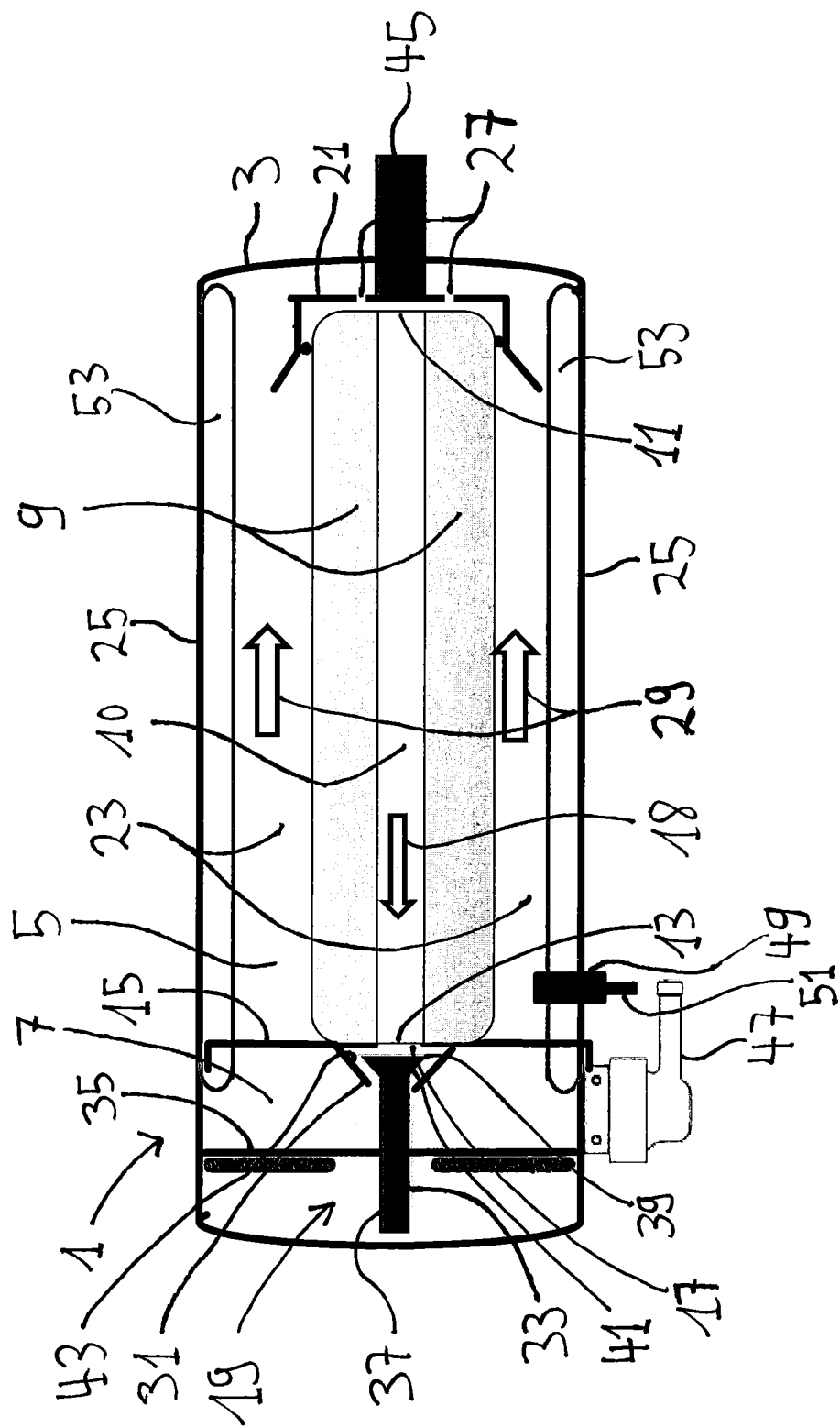

CHEMICAL OXYGEN GENERATOR WITH BIMETAL REACTION CONTROL

CROSS-REFERENCE TO RELATED APPLICATION

This application claims the benefit of and priority to U.S. Provisional Application No. 61/665,486 filed on Jun. 28, 2012, the contents of which are incorporated herein by reference.

FIELD OF THE INVENTION

The invention relates to a regulation device for a source of breathable gas, comprising a reaction medium adapted to perform an exothermic reaction for the production of breathable gas, the reaction medium surrounding an interior reaction volume having a breathable gas outlet. The invention further relates to a method for regulating a source of breathable gas, comprising the step of initiating an exothermic reaction of a reaction medium for the production of breathable gas, the reaction medium surrounding an interior reaction volume having a breathable gas outlet, wherein the breathable gas is flowing through the breathable gas outlet.

BACKGROUND OF THE INVENTION

Oxygen sources for production and provision of breathable oxygen are generally known from the art. Oxygen can be produced in many different ways. In cases of emergencies in aircrafts, aircraft passengers need to be supplied with emergency oxygen in order to be protected from pressure drops of the aircraft cabin pressure. The emergency oxygen may be provided by chemical oxygen generators (COGs), wherein the oxygen is generated by high-temperature decomposition of sodium chlorate.

A problem associated with such chemical oxygen generators is the chemical reaction to not run in a reproducible manner inside the oxygen generator. The inventor has recognized that external influences like cabin pressure, cabin temperature may significantly influence the speed of the chemical reaction and thus result in too much or to little oxygen being produced in the chemical oxygen generator. Particularly in an emergency situation the cabin temperature and cabin pressure may significantly vary. Further, the speed of the chemical reaction and thus the amount of oxygen produced per time unit may depend on the age of the sodium chlorate and further depend on manufacturing effects of the sodium chlorate component. Such effects may further influence the amount of oxygen produced per time unit in the chemical reaction. All these internal and external effects may adversely affect the oxygen production and result in insufficient delivery of oxygen or insufficient delivery time of oxygen.

SUMMARY OF THE INVENTION

It is an object of the present invention to enhance existing sources of breathable gas and to provide an emergency oxygen supply which overcomes these problems.

This object is achieved by a regulation device as mentioned above according to independent claim 1. The regulation device comprises a flow regulator arranged at the breathable gas outlet of the interior reaction volume and adapted to regulate the flow of breathable gas through the breathable gas outlet depending on a temperature of the regulation device.

It has been discovered by the invention that oxygen sources for the use of emergency oxygen supply, in particular chemical oxygen generators, are inefficient with regard to the amount of oxygen produced and supplied to the passenger. In certain phases of the chemical reaction, more oxygen than actually needed by the passenger is produced. The present invention addresses this problem by providing a limitation of excess oxygen production. This limitation is achieved by the flow regulator arranged at the breathable gas outlet of the interior reaction volume. Depending on the temperature of the regulation device, the flow of oxygen from the interior reaction volume surrounded by reaction medium is regulated.

The expression "having a breathable gas outlet" is preferably to be understood as a breathable gas outlet of the interior reaction volume. However, it can also be understood as a breathable gas outlet of another part of the regulation device, as long as the regulation by means of the flow regulator affects the conditions, e.g. the pressure, of the exothermic reaction.

When it is stated in the context of the present invention that an action is depending on a temperature of an object, this can be understood in a way that the action is depending only on the temperature of this object but it can also be understood in a way that the action is depending on the temperature of further objects or media. Since in a non-equilibrium state, an object may have different temperatures at different locations of the object, the term "temperature of the regulation device" can be understood to mean the overall or average temperature of the regulation device but also the temperature at a predetermined location of the regulation device. Preferably, the term "temperature of the regulation device" can be understood such that the flow regulator is adapted to regulate the flow of breathable gas through the breathable gas outlet depending on the temperature of the flow regulator itself, in particular a certain part of the flow regulator. Further preferably, the term "temperature of the regulation device" can be understood such that the flow regulator is adapted to regulate the flow of breathable gas through the breathable gas outlet depending on the temperature of the reaction medium. The term "temperature of the regulation device" can even further preferably be understood as the temperature within a housing in which the reaction medium is seated, in particular a temperature of the reaction medium or a temperature of the flow regulator being arranged close to the reaction medium.

The regulation of the flow of breathable gas through the breathable gas outlet of the reaction medium can be understood as a regulation of the flow of breathable gas to the passenger. It can preferably be understood as a regulation of the flow of breathable gas in a way that the flow of breathable gas from the breathable gas outlet is throttled and, thereby, the pressure in the volume surrounding the reaction medium, in particular the pressure in the interior reaction volume is increased. Such an increase of pressure leads to a negative shift of the reaction rate, in particular a deceleration of the exothermic reaction for oxygen production. This deceleration of the reaction for oxygen production limits the excess oxygen production and increases the duration of oxygen supply to passengers.

The term "oxygen source" can preferably be understood as a chemical oxygen generator (COG), wherein the reaction medium preferably substantially comprises sodium chlorate ($NaClO_3$) as well as iron (Fe). When the reaction for the production of oxygen is initiated, the sodium chlorate reacts with the iron to sodium chloride, iron(II) oxide (FeO) and oxygen. Such a reaction may take place at temperatures of up to 260° C. as well as high pressures. Preferably, barium peroxide (BaO2) is used to absorb the chlorine being a product of the reaction. The reaction is often initiated by an ignition system which is triggered by a passenger pulling an oxygen supply mask from a passenger service unit.

According to a first preferred embodiment of the present invention, the flow regulator comprises or consists of a valve body actuated by a bimetal element, preferably a bimetallic arm. Preferably, the valve body consists of an elongate member, such as a rod, and a head portion, the head portion preferably having conical shape. The elongate member is mechanically connected to a bimetallic arm in a way that a change of the form of the bimetallic arms leads to an actuation of the elongate member. Depending on the direction of actuation, the head portion is moved closer or further away from a valve seat and, thereby, the flow of breathable gas through the flow regulator is decreased or increased. This can preferably be understood as follows: when the temperature increases, the bimetallic arm changes its form in a way that the head portion moves closer to the valve seat and, thereby, throttles the flow of breathable gas through the flow regulator. In the other hand, when the temperature decreases, the bimetallic arm changes its form in a way that the head portion moves further away from the valve seat and, thereby, increases the flow of breathable gas through the flow regulator.

As mentioned above, a decreasing flow of breathable gas through the flow regulator leads to a pressure increase in the interior reaction volume and, thereby, to a decrease of the reaction rate.

According to a second preferred embodiment of the present invention, the flow regulator comprises or consists of a valve body actuated by a shape-memory alloy element. The valve body, as mentioned above, preferably consists of an elongate member and a head portion. By use of a shape-memory alloy element, the flow regulator may reach two flow states corresponding to two states of the shape-memory alloy. In other words, a first state is reached when the temperature of the shape-memory alloy is lower than a predetermined temperature value. In this first state, the flow regulator provides for a first amount of flow of breathable gas. A second state is reached when the temperature of the shape-memory alloy is higher than the predetermined temperature value. In this second state, the flow regulator provides for a second amount of flow, which is smaller than the first amount of flow. By this second preferred embodiment, a digital switch between two flow states is achieved. This further simplifies the design of the flow regulator. Further preferably, shape-memory alloy can be designed in a way that the head portion can be prevented from directly abutting the valve seat and, thereby, preventing the flow regulator to completely close and stop the flow of breathable gas to an oxygen supply mask.

According to a third preferred embodiment of the present invention, the regulation valve comprises a housing having a breathable gas outlet, wherein the reaction medium is arranged within the housing and has substantially annular shape surrounding the interior reaction volume, and comprising an exterior volume being arranged between the reaction medium and a wall of the housing, wherein the regulation device is adapted to direct a flow of reaction gas through the exterior volume on its way to a reaction gas inlet of the interior reaction volume. Preferably, the design of the housing and reaction medium can be understood in a way that a flow of reaction gas is forced to flow through the exterior volume on its way to the reaction gas inlet. Thereby, environmental temperature effects can be reduced.

Further preferably, the housing comprises two separated chambers, namely a first chamber in which the reaction medium is seated and a second chamber in which the flow regulator is seated. The flow of breathable gas is directed from the interior reaction volume through the flow regulator into the second chamber. A breathable gas outlet for directing the breathable gas to the passenger supply mask is formed at the second chamber.

Additionally, a conduct may be arranged between the second chamber and the exterior volume which provides for a predetermined flow of gas from the second chamber to the exterior and, thereby, provides for a flow of reaction gas through the exterior volume as mentioned with regard to the third preferred embodiment of the present invention.

With regard to the two separate chambers, the term "temperature of the regulation device" can also be understood such that the flow regulator is adapted to regulate the flow of breathable gas through the breathable gas outlet depending on the temperature in the first and/or second chamber.

In an enhancement of the third preferred embodiment of the present invention, the regulation device comprises a pressure relief valve adapted to release breathable gas from the housing if a predetermined pressure value is exceeded, preferably the pressure relief valve being connected to a conduct adapted to direct the breathable gas released by means of the pressure relief valve to an aircraft cabin. This provides for a safety means for preventing high pressure values which might lead to a safety risk. The conduct can be provided by a hose or pipe.

In a fourth preferred embodiment of the present invention, the flow regulator is adapted to regulate the flow of breathable gas through the breathable gas outlet depending on the ambient temperature of the aircraft. In addition to a dependency of the flow regulation on the temperature of the regulation device, as defined in the independent claim 1, also an ambient temperature of an object or medium can be the factor on which the flow regulation depends. Preferably, the flow regulation depends on the ambient temperature of the aircraft, i.e. the temperature of the air surrounding the aircraft. This provides for a dependency of the flow regulation on the environment of the aircraft. This has the advantage, that the supply of oxygen is adapted to the environmental conditions of the aircraft, such as height, temperature, weather, etc.

According to an enhancement of the fourth preferred embodiment of the present invention, the flow regulator is adapted to throttle the flow of breathable gas through the breathable gas outlet if the temperature of the regulation device and/or the ambient temperature is increased. A design according to this enhancement allows for a purposeful operation of the regulation device in a predetermined "direction", namely a throttling (decrease) of the flow of breathable gas through the breathable gas outlet when the temperature of the regulation device and/or the ambient temperature increases.

The object of the present invention is also achieved by a chemical oxygen generator system for the provision of breathable gas in an aircraft, comprising a regulation device of the above described kind.

The object of the present invention can also be achieved by a method according to independent claim 8.

The method according to the present invention is characterized by the step of regulating the flow of breathable gas, which is flowing through a breathable gas outlet, by means of a regulation device depending at least on the temperature of the regulation device.

According to a first preferred embodiment of the method according to the present invention, the regulating is achieved by means of a flow regulator comprising or consisting of a valve body actuated by a bimetal, preferably a bimetallic arm.

In a second preferred embodiment, the method according to the present invention comprises the step of directing a flow of reaction gas, which is flowing to a reaction gas inlet of the interior reaction volume, through an exterior volume, the exterior volume being arranged between the reaction medium and a wall of a housing having a breathable gas outlet.

In a third preferred embodiment, the method according to the present invention comprises the step of regulating the flow of breathable gas through the breathable gas outlet depending on the ambient temperature, preferably an ambient temperature of the aircraft.

According to an enhancement of third preferred embodiment, the method comprises the step of throttling the flow of breathable gas through the breathable gas outlet if the temperature of the regulation device and/or the ambient temperature increases.

With respect to the advantages, embodiments and details of embodiments of the method according to the present invention, it is referred to the preceding description of the respective features of the regulation device and its embodiments.

BRIEF DESCRIPTION OF THE DRAWING

A preferred embodiment of the invention is described in connection with the FIGURE which illustrates an embodiment of the regulation device according to the present invention.

DETAILED DESCRIPTION OF THE DRAWING

The FIGURE shows an embodiment of a regulation device 1 according to the present invention in a cross-sectional side view. The regulation device 1 operates according to an embodiment of the method according to the present invention. The regulation device 1 is seated within a housing 3 having a first chamber 5 and a second chamber 7. A reaction medium 9 is seated within the first chamber 5. The reaction medium 9 has annular shape surrounding an interior reaction volume 10 having a reaction gas inlet 11 and a breathable gas outlet 13. A wall 15 separates the first chamber 5 and second chamber 7, the wall 13 having an aperture 17 for flow 18 of breathable gas from the reaction gas outlet 13 to a flow regulator 19. The reaction medium 9 abuts the wall 15 at the breathable gas outlet 13 and is seated partially within a support 21.

The reaction medium 9 consists of sodium chlorate (NaClO$_3$) having iron fillings. When the reaction for the production of oxygen is initiated, the sodium chlorate reacts with the iron to sodium chloride, iron(II) oxide (FeO) and oxygen.

An exterior volume 23 is formed between the reaction medium 9 and an annular wall 25 of the housing 3. The support 21 has an aperture 27 for allowing a flow 29 of reaction gas to pass when flowing through the exterior volume 23 on its way to the interior reaction volume 10.

The flow regulator 19 is arranged within the second chamber 7 of the housing 3 and consists of a valve seat 31, a valve body 33 and a bimetallic arm 35. The valve seat 31 extends from the wall 15 having a substantially conical shape. The valve body 33 consists of a rod 37 and a head portion 39 having a substantially conical surface 41 corresponding to a conical surface 43 of the valve seat 31.

The regulation device 1 has an ignitor 45 for triggering an exothermic reaction of the reaction medium 9 for the production of breathable oxygen, in a method step a). The ignition is started when a passenger pulls an oxygen supply mask from a passenger service unit. The exothermic reaction produces the flow 18 of breathable gas to the breathable gas outlet 13. The housing 3 has a breathable gas outlet 47 for directing the breathable gas to a passenger in an aircraft (not shown in the FIGURE).

In a method step b), when the temperature in the first chamber 5 and second chamber 7 increases, the bimetallic arm 35 changes its form, i.e. the bimetallic arm bends to the left (as seen in viewing direction of the FIGURE). Thereby, valve body 33 moves horizontally to the left (as see in viewing direction) and the head portion 39 moves closer to the valve seat 31. Thereby, the flow of breathable gas through the flow regulator 19 is throttled and, at the same time, the pressure within the first chamber 5, in particular the interior reaction volume 10 increases. An increase of the pressure in the first chamber 5 leads to a negative shift of the exothermic reaction, i.e. the exothermic reaction is slowed down.

The first chamber 5 further has a pressure relief valve 49 arranged at the housing 3. The pressure relief valve 49 releases breathable gas from the housing 3 if a predetermined pressure value is exceeded. The pressure relief valve 49 is connected to a conduct 51 for directing the breathable gas released by means of the pressure relief valve 49 to the oxygen supply mask arranged in an aircraft cabin where the passengers are seated. Furthermore, an annular isolation layer 53 is formed at the annular wall 25 for preventing high temperatures within the housing 3 to be transferred to the environment of the housing 3.

REFERENCE NUMERALS 1 regulation device
3 housing
5 first chamber
7 second chamber
9 reaction medium
10 interior reaction volume
11 reaction gas inlet
13 breathable gas outlet
15 wall
17 aperture
18 flow
19 flow regulator
21 support
23 exterior volume
25 annular wall
27 aperture
29 flow
31 valve seat
33 valve body
35 bimetallic arm
37 rod
39 head portion
41 conical surface
43 conical surface
45 ignitor
47 breathable gas outlet
49 pressure relief valve
51 conduct
53 isolation layer

The invention claimed is:

1. A regulation device for a source of breathable gas, comprising:
   a reaction medium comprising sodium chlorate having iron fillings, the reaction medium adapted to perform an exothermic reaction for production of oxygen, the reaction medium having an annular shape and surrounding an interior reaction volume having a reaction gas inlet and a first breathable gas outlet;
   a flow regulator arranged at the first breathable gas outlet and adapted to regulate a flow of oxygen through the first breathable gas outlet depending at least on a temperature of the regulation device and to throttle the flow of oxygen through the first breathable gas outlet if the temperature of the regulation device is increased;
   a rigid housing comprising a substantially tubular shape and comprising a second breathable gas outlet; and
   an exterior volume arranged radially outwardly between the reaction medium and an annular wall of the housing, the exterior volume surrounding the reaction medium radially, wherein the regulation device is adapted to direct a flow of reaction gas through the exterior volume towards the reaction gas inlet of the interior reaction volume.

2. A regulation device according to claim 1, wherein the flow regulator comprises a valve body actuated by a bimetal element.

3. A regulation device according to claim 1, comprising:
   a pressure relief valve adapted to release the oxygen from the housing if a predetermined pressure value is exceeded.

4. A regulation device according to claim 1, wherein the flow regulator is adapted to regulate the flow of the oxygen through the first breathable gas outlet depending on an ambient temperature of an aircraft.

5. A regulation device according to claim 4,
   wherein the flow regulator is adapted to throttle the flow of the oxygen through the first breathable gas outlet if the ambient temperature of the aircraft is increased.

6. Method for regulating a source of breathable gas, comprising the steps of:
   a) initiating an exothermic reaction of a reaction medium comprising sodium chlorate having iron fillings for production of oxygen, the reaction medium having an annular shape and surrounding an interior reaction volume having a reaction gas inlet and a first breathable gas outlet, wherein the oxygen is flowing in a first direction through an exterior volume formed circumferentially around the reaction medium, from the exterior volume through the reaction gas inlet into the interior reaction volume, through the interior reaction volume in a second direction opposite the first direction and through the first breathable gas outlet, and
   b) regulating a flow of the oxygen, which is flowing through the first breathable gas outlet, by a regulation device depending at least on a temperature of the regulation device.

7. Method according to claim 6, wherein the regulating is achieved by a flow regulator comprising a valve body actuated by a bimetal.

8. Method according to claim 6, comprising the step of:
   directing a flow of reaction gas, which is flowing to a reaction gas inlet of the interior volume, through the exterior volume, the exterior volume being arranged between the reaction medium and a wall of a housing having a second breathable gas outlet.

9. Method according to claim 6, comprising the step of:
   regulating the flow of the oxygen through the first breathable gas outlet depending on an ambient temperature of an aircraft.

10. Method according to claim 9, comprising the step of:
    throttling the flow of the oxygen through the first breathable gas outlet if the temperature of the regulation device and/or the ambient temperature of the aircraft increases.

11. A regulation device according to claim 1, wherein the flow regulator consists of a valve body actuated by a bimetal element.

12. A regulation device according to claim 2, wherein the bimetal element is a bimetallic arm.

13. A regulation device according to claim 11, wherein the bimetal element is a bimetallic arm.

14. A regulation device according to claim 3, wherein the pressure relief valve is connected to a conduit adapted to direct the oxygen released by the pressure relief valve to an aircraft cabin.

15. A regulation device for a source of breathable gas, comprising:
    a rigid housing comprising a substantially tubular shape that includes an exterior sidewall defining an inner cavity and a gas outlet in fluid communication with the inner cavity;
    a reaction medium positioned within the inner cavity, the reaction medium defining an interior reaction volume having an inlet and an outlet, the reaction medium and housing defining an exterior reaction volume between the reaction medium and the exterior sidewall and in fluid communication with the interior reaction volume;
    a flow regulator arranged between the outlet of the inner reaction volume and the gas outlet of the housing, the flow regulator adapted to selectively throttle a flow of the breathable gas from the outlet of the reaction medium to the gas outlet of the housing based on a temperature of the regulation device; and
    an ignitor adapted to activate the reaction medium, wherein an activation of the reaction medium produces the breathable gas.

16. A regulation device according to claim 15, wherein the housing further comprises an interior wall within the inner cavity, wherein the interior wall defines a first chamber and a second chamber within the inner cavity, wherein the reaction medium is positioned within the first chamber, and wherein the flow regulator is positioned within the second chamber.

17. A regulation device according to claim 16, wherein the housing further comprises a support within the inner cavity, wherein the reaction medium is supported by the support within the inner cavity.

18. A regulation device according to claim 17, wherein the interior wall defines an aperture in fluid communication with the outlet of the interior reaction volume, and wherein the flow regulator comprises:
    a valve seat extending from the interior wall;
    a valve body selectively movable through the valve seat; and
    a bimetallic arm connected to the valve body, the bimetallic arm elastically deformable between a first state and a second state.

19. A regulation device according to claim 15, wherein the housing further comprises an isolation layer at the exterior sidewall within the inner cavity.

* * * * *